United States Patent [19]

Stetter et al.

[11] Patent Number: 4,693,978

[45] Date of Patent: Sep. 15, 1987

[54] TYPE II RESTRICTION ENDONUCLEASE MAEI, A PROCESS FOR OBTAINING IT AND THE USE THEREOF

[75] Inventors: Karl O. Stetter, Regensburg; Rüdiger Schmitt, Niedergebraching, both of Fed. Rep. of Germany

[73] Assignee: Boehringer Mannheim GmbH, Mannheim-Waldhof, Fed. Rep. of Germany

[21] Appl. No.: 655,468

[22] Filed: Sep. 28, 1984

[30] Foreign Application Priority Data

Jan. 18, 1984 [DE] Fed. Rep. of Germany ....... 3401617

[51] Int. Cl.$^4$ .......................... C12N 9/22; C12N 9/16; C12N 15/00; C12R 1/01
[52] U.S. Cl. .................................... 435/199; 435/196; 435/172.3; 435/822
[58] Field of Search ............... 435/195, 196, 199, 822, 435/91, 172.3

[56] References Cited

PUBLICATIONS

Schmid, K. et al., *Nuc. Acids Res.*, vol. 12, No. 6, pp. 2619–2628, Mar., 1984.

Balch, W. et al., *Micro. Revs.*, vol. 43, No. 2, pp. 260–264, 285 and 286, 1979.

*Primary Examiner*—Thomas G. Wiseman
*Assistant Examiner*—Jayme A. Huleatt
*Attorney, Agent, or Firm*—Felfe & Lynch

[57] ABSTRACT

The present invention provides a restriction endonuclease, characterized by the palindromic recognition sequence:

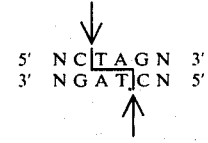

and the cleavage position defined by the arrows.

The present invention also provides a process for obtaining this new restriction endonuclease.

6 Claims, No Drawings

TYPE II RESTRICTION ENDONUCLEASE MAEI, A PROCESS FOR OBTAINING IT AND THE USE THEREOF

The present invention is concerned with a new Type II restriction endonuclease MaeI, with a process for obtaining it and with the use thereof.

Type II restriction endonucleases are endodeoxyribonucleases which are able to recognize and cleave certain DNA at nucleotide sequences. Phosphodiester bridges are thereby hydrolysed in the target sequence, namely one in each polynucleotide strand. Therefore, Type II restriction endonucleases are valuable for the analysis of DNA molecules.

Specific Type II restriction endonucleases are admittedly already known for numerous nucleotide sequences, but there is still a need for provision of further Type II restriction endonucleases specific for such recognition for which restriction endonucleases have not been recognized.

Therefore, it is an object of the present invention to provide a new restriction endonuclease which is able specifically to recognize and cleave a sequence hitherto not recognized by any such enzyme.

Thus, according to the present invention, there is provided a restriction endonuclease which is characterized by a palindromic recognition sequence:

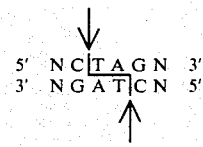

and the splitting position defined by the arrow.

The new Type II restriction endonuclease according to the present invention, which in the following is called MaeI, has a temperature optimum of from 45° to 48° C. and a pH optimum at 8.0/45° C. in Tris/HCl buffer. Further optimum reaction parameters are 250 mM sodium chloride, 12 to 18 mM $mg^{2+}$, 6 to 12 mM 2-mercaptoethanol. The presence of magnesium ions is essential for the activity of the enzyme.

As mentioned above, the enzyme acts upon palindromic structures and thus recognizes a self-complementary structure in which the complementary strand of the DNA has the identical sequence in the opposite-running direction.

The recognition sequence and the point of cleavage of the enzyme can be ascertained as follows: a plasmid pBR322 is completely digested with HinfI. The HinfI fragments B and C (517 bp and 506 bp, respectively) are isolated, their 3'-ends are marked with alpha-[$^{32}$P]-dATP and Klenow polymerase and subsequently cleaved with AluI. From the marked fragments hereby resulting, there is isolated and sequenced the 330 bp fragment (pBR322, position 3037 to 3366, length of the fragment including single strand ends).

An aliquot of the 330 bp fragment is cleaved with the enzyme according to the present invention, resulting in two fragments. The cleavage position 3223 lying close to the 3' labeled end was determined.

The length of the HinfI/MaeI fragment is determined in sequence gels. The HinfI/MaeI fragment thereby runs in the gel like the "C" of the sequence ladder in the recognition sequence 5'-CTAG-3'. Therefore, it terminates with the nucleotide T of the recognition sequence. Thus, the cleavage position of MaeI is between nucleotide C and T.

The new endonuclease MaeI according to the present invention is obtained by culturing Methanococcus aeolicus DSM 2835 and recovering the enzyme from the cells. For the recovery, there can be used conventional biochemical purification methods, whereby, in the particular fractions obtained, the presence of the enzyme can be ascertained on the basis of the cleavage of its recognition sequence. As substrate, there can be used, for example, pBR322-DNA. The DNA fragments obtained are separated electrophoretically in agarose gels in the buffer systems usual for fragment separation in the presence of ethidium bromide.

The microorganisms used for obtaining the enzyme grows anaerobically in Medium III (Microbiol. Reviews, 43, 260–296/1979) on $H_2/CO_2$ or on formate. It forms regular to irregular cocci of about 2 μm diameter, individually and in pairs. On agar, round, convex, pale ochre-coloured colonies are formed with about 2 mm diameter. The microorganism is gram negative. The cell integument consists of protein subunits. Growth takes place at temperatures between 25° and 50° C., the temperature optimum being 45° C. (2 hours duplication time). Growth takes place in the presence of 1.5 to 5% and optimally of 4% sodium chloride. The DNA base composition is about 28.6% G+C. Therefore, the microorganism differs from known Methanococci by a somewhat lower GC content of DNA, by an optimum growth temperature of 45° C., by the markedly larger cells and by the presence of new restriction enzymes. Methanococcus aeolicus has beed deposited at the Deutsches Sammlung von Mikroorganismen, Gesellschaft für Biotechnologische Forschung GmbH, Grisebachstrasse 8, 3400 Göttingen, Federal Republic of Germany, and bears Accession Number DSM 2835.

In a preferred embodiment of the process according to the present invention, the cells are digested, the extract is mixed with polyethyleneimine up to a concentration of 0.65%, the precipitate is separated off and the fraction precipitating out from the supernatant up to 60% ammonium sulphate saturation is recovered.

For the digestion, there can be used conventional mechanical and chemical methods, for example high pressure dispersion, ultrasonics or enzymatic digestion.

Further purification of the ammonium sulphate fraction containing the new enzyme is preferably conducted by molecular sieve fractionation, chromatography over anion exchangers and over cation exchangers, as well as subsequent affinity chromatography. As molecular sieve material, there has proved to be useful the product commercially available under the trade name Ultrogel AcA 34, this being an acrylamide/agarose heteropolymer of 3% acrylamide and 4% agarose. As anion exchangers, there can be used carrier materials based on sepharose, cellulose or synthetic polymers modified with diethylaminoethyl substituents for example the product available from Pharmacia, Uppsala, Sweden, under the trade name DEAE-Sephacel.

As cation exchangers, there are preferably used phosphate group-containing substances, preferably carbohydrates, for example cellulose phosphate and the like. For the affinity chromatography, carrier-fixed heparin, for example heparin-sepharose, has proved to be especially useful.

The following examples are given for the purpose of illustrating the present invention:

EXAMPLE 1

*Methanococcus aeolicus* DSM 2835 is allowed to grow anaerobically in minimal formate medium, which is described hereinafter, at 45° C. for 3 days and then harvested in the stationary phase. 35 g of the cell paste thus obtained are suspended in 70 ml digestion buffer (40 mM Tris/HCl, pH 8.0/4° C.; 0.1 mM EDTA (ethylenediamine-tetraacetic acid); 7 mM 2-mercaptoethanol and 0.2 mM PMSF (phenylmethanesulphonyl fluoride). The cells are then digested twice by high pressure dispersion in a pre-cooled pressure cell at 1100 bar. $\triangleq$ 16,000 PSI.

To the digestion suspension ammonium chloride is added to a final concentration of 0.3M, subsequently, 7 ml 10% polyethyleneimine solution are added thereto up to a final concentration of 0.65% v/v. After leaving to stand for 30 minutes at 4° C., the precipitate formed is centrifuged for 60 minutes at 27,300 g or 23,000 g and discarded. The supernatant is mixed with solid ammonium sulphate up to 60% saturation. The ammonium sulphate precipitate is, after 16 hours at 4° C., centrifuged off at 4° C. for 60 minutes at 27,300 g or 23,000 g.

The minimal medium has the following composition: dissolve:

|  | g/liter |
| --- | --- |
| KCl | 0.32 g |
| $MgCl_2.6H_2O$ | 2.75 g |
| $MgSO_4.7H_2O$ | 3.45 g |
| $NH_4Cl$ | 0.25 g |
| $CaCl_2.2H_2O$ | 0.15 g |
| $K_2HPO_4$ | 0.15 g |
| NaCl | 18 g |
| mineral elixir (see below) | 10 ml |
| $Fe(NH_4)_2(SO_4)_2.7H_2O$ | 2 mg |
| $NaHCO_3$ (added at end) | 5.5 g |
| resazurin 0.1% | 1 ml |
| sodium formate | 15 g |
| sodium tungstate | 3.3 mg | add 50 ml reducing agent consisting of 12.5 g/liter sodium sulphide, nitrogen being bubbled through, 75 ml of freshly prepared 1N sodium hydroxide solution and 1 ml 0.1% resazurin, adjust the pH value to 6.9 with formic acid, make up to 1 liter and allow nitrogen to bubble through.

The mineral elixir referred to above has the following composition:

|  | g/liter |
| --- | --- |
| Titriplex I | 1.5 g |
| $MgSO_4.7H_2O$ | 3.0 g |
| $MnSO_4.2H_2O$ | 0.5 g |
| NaCl | 1.0 g |
| $FeSO_4.7H_2O$ | 0.1 g |
| $CoSO_4$ or $CoCl_2$ | 0.1 g |
| $CaCl_2.2H_2O$ | 0.1 g |
| $ZnSO_4$ | 0.1 g |
| $CuSO_4.5H_2O$ | 0.01 g |
| $KAl(SO_4)_2$ | 0.01 g |
| $H_3BO_3$ | 0.01 g |
| $Na_2MoO_4.2H_2O$ | 0.01 g |
|  | slowly adjust pH value to 6.5 with 5 N KOH |

EXAMPLE 2

The ammonium sulphate precipitate obtained according to example 1 is taken up with TEMG buffer (40 mM Tris/HCl, pH 8.0/4° C.; 0.1 mM EDTA; 7 mM 2-mercaptoethanol; 10% v/v glycerol) and 0.5M sodium chloride and applied to an Ultrogel AcA 34 molecular sieve column of 3×100 cm. This column is eluted with TEMG buffer +0.5M sodium chloride and the eluate fractions with MaeI activity are combined.

The combined eluate fractions are chromatographed on an anion exchange column (DEAE-Sephacel; 2×10 cm) equilibrated with TEMG buffer. After washing with two column volumes of TEMB buffer, the enzyme is eluted with a linear gradient of 0 to 1M sodium chloride in TEMG. The enzyme appears in the fractions with 0.1 to 0.3M sodium chloride. The fractions are combined and dialysed against TEMG buffer. The dialysate is chromatographed on a cation exchanger column (cellulose phospate P 11; 1×10 cm) equilibrated with TEMG buffer. Washing and elution take place as in the case of the anion exchanger column. MaeI is eluted between 0.4 and 0.6M sodium chloride. The combined enzyme-containing fractions are again dialysed against TEMG buffer and the dialysate chromatographed on an affinity chromatography column (Heparin-Sepharose CL-6B; 1×5 cm) equilibrated with TEMG buffer. Washing and elution again take place as described in the case of the anion exchanger column. MaeI is eluted between 0.4 and 0.6M sodium chloride. The active fractions are combined, dialysed against 20 mM Tris/HCl buffer, pH 8.0, at 4° C., containing 0.1 mM EDTA, 10 mM 2-mercaptoethanol, 100 mM sodium chloride, 50 vol.% glycerol, 0.01 vol.% Triton X100, and stored at −20° C. The activity is about 10,000 U MaeI (activity definition: 1 U=1 μg pBR322-DNA/hour at 45° C. completely cleaved).

DETERMINATION OF ACTIVITY

Into a mixture of 5 μl incubation buffer containing 0.03M Tris/HCl, pH 8.0/45° C., 1.25M sodium chloride, 0.07M magnesium chloride, 0.035M 2-mercaptoethanol and 0.05 vol.% Triton X 100, are introduced 14 μl water and 5 μl pBR322-DNA (4 OD/ml), as well as 1 μl MaeI solution (1 U/μl). The solution is kept for 1 hour at 45° C., cooled on ice and mixed with 5 μl of a cold stop solution containing 7M urea, 20% w/v sucrose, 0.06M EDTA and 0.01% w/v bromophenol blue. It is then separated electrophoretically on 1% agarose gel for 3 to 4 hours at 100 V. The bands obtained are identified in comparison with suitable DNA length standards.

We claim:

1. A restriction endonuclease capable of recognizing and cleaving a DNA sequence at a position indicated by the arrows:

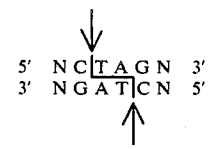

2. The restriction endonuclease of claim 1 wherein said endonuclease is characterized by a temperature optimum between 45° and 48° C. and a pH optimum at 8.0/45° C. in Tris HCl buffer.

3. A process for obtaining the restriction endonuclease of claim 1 comprising the steps of culturing *Methanococcus aeolicus* DSM 2835 cells and recovering the restriction endonuclease from the cells.

4. The process of claim 3 comprising recovering the endonuclease from the cells of *Methanococcus aeolicus* by digesting the cells to release an extract therefrom, mixing the extract released from the digested cells with polyethylenimine up to a concentration of 0.65% v/v, separating off insolubles and leaving a supernatant, mixing the supernatant with ammonium sulphate in an amount of up to 60% saturation to form a precipitated fraction and recovering the precipitated fraction.

5. The process of claim 4, further comprising purifying the ammonium sulphate precipitated fraction by at least one process selected from the group consisting of molecular sieve fractionation, chromatography over a weakly basic anion exchanger, chromatography over a weakly acidic cation exchanger, and affinity chromatography.

6. The process of claim 5, wherein carrier-fixed heparin is used for the affinity chromatography.

* * * * *